(12) United States Patent
Aflatoon

(10) Patent No.: US 10,869,734 B2
(45) Date of Patent: Dec. 22, 2020

(54) SELF-ORIENTING SURGICAL LIGHT PANEL

(71) Applicant: Kamran Aflatoon, Corona del Mar, CA (US)

(72) Inventor: Kamran Aflatoon, Corona del Mar, CA (US)

( * ) Notice: Subject to any disclaimer, the term of this patent is extended or adjusted under 35 U.S.C. 154(b) by 0 days.

(21) Appl. No.: 15/668,587

(22) Filed: Aug. 3, 2017

(65) Prior Publication Data

US 2018/0036094 A1 Feb. 8, 2018

Related U.S. Application Data

(60) Provisional application No. 62/370,466, filed on Aug. 3, 2016.

(51) Int. Cl.

| | |
|---|---|
| *A61B 90/30* | (2016.01) |
| *F21V 33/00* | (2006.01) |
| *F21S 2/00* | (2016.01) |
| *H05B 47/10* | (2020.01) |
| *H05B 47/19* | (2020.01) |
| *A61B 17/00* | (2006.01) |

(Continued)

(52) U.S. Cl.
CPC .............. *A61B 90/30* (2016.02); *F21S 2/00* (2013.01); *F21V 33/0052* (2013.01); *H05B 47/10* (2020.01); *H05B 47/19* (2020.01); *A61B 2017/00017* (2013.01); *A61B 2017/00221* (2013.01); *A61B 2017/00398* (2013.01); *A61B 2017/00438* (2013.01); *A61B 2017/00442* (2013.01); *A61B 2090/309* (2016.02); *F21S 8/026* (2013.01); *F21V 21/15* (2013.01); *F21W 2131/205* (2013.01); *F21Y 2115/10* (2016.08)

(58) Field of Classification Search
CPC ........... A61B 90/30–35; H05B 37/0245–0272; F21W 2131/20–208
See application file for complete search history.

(56) References Cited

U.S. PATENT DOCUMENTS 6,803,727 B2 * 10/2004 Laerum ................. A61B 90/35
 315/129
8,502,480 B1 * 8/2013 Gerszberg ............. H05B 37/02
 315/312

(Continued)

*Primary Examiner* — Nicholas J Plionis
*Assistant Examiner* — Steven J Cotroneo
(74) *Attorney, Agent, or Firm* — Royal W. Craig; Gordon Feinblatt LLC

(57) ABSTRACT

A lighting system for an operating room wherein machine-controlled light sources are Bluetooth™-enabled to allow them to locate and track the movement of a device worn on the hand or wrist of a surgeon or other operating room personnel. In preferred embodiments, the system described herein will accommodate light source tracking for multiple surgeon-worn devices worn by one or more wearers. The system is capable of toggling between modes of following the wearer's movement and focusing on a single point determined by the wearer, where mode swapping can be controlled by the surgeon from the device itself. The system preferably accommodates the adjustment of multiple characteristics of the light source, such as light intensity, from the hand or wrist device. A periphery ribbon may also be used to control the direction of light sources. Applications of the invention y stretch to other fields such as construction or theater lighting.

16 Claims, 3 Drawing Sheets

(51) Int. Cl.
*F21Y 115/10* (2016.01)
*F21S 8/02* (2006.01)
*F21W 131/205* (2006.01)
*F21V 21/15* (2006.01)

(56) References Cited

U.S. PATENT DOCUMENTS

| | | | | |
|---|---|---|---|---|
| 9,035,555 B2* | 5/2015 | Fornasiero | | A61B 90/35 315/129 |
| 9,560,721 B2* | 1/2017 | Luostarinen | | A61B 50/28 |
| 9,986,625 B2* | 5/2018 | Yadav | | H05B 37/0281 |
| 2010/0081926 A1* | 4/2010 | Hyde | | A61B 5/0084 600/431 |
| 2011/0015492 A1* | 1/2011 | Mangiardi | | A61B 90/35 600/249 |
| 2012/0155057 A1* | 6/2012 | McNeill | | A61N 5/062 362/33 |
| 2012/0180180 A1* | 7/2012 | Steve | | A61F 9/067 2/12 |
| 2012/0217882 A1* | 8/2012 | Wong | | F21V 23/0464 315/185 R |
| 2013/0310652 A1* | 11/2013 | Barsoum | | A61B 90/30 600/249 |
| 2014/0194702 A1* | 7/2014 | Tran | | A61B 8/06 600/301 |
| 2015/0035437 A1* | 2/2015 | Panopoulos | | F21V 14/02 315/112 |
| 2015/0334802 A1* | 11/2015 | Ryu | | H05B 33/0809 315/193 |
| 2015/0366039 A1* | 12/2015 | Noori | | H05B 37/0272 315/307 |
| 2015/0369455 A1* | 12/2015 | Nieminen | | F21S 2/005 362/428 |
| 2016/0310074 A1* | 10/2016 | Kim | | A61B 5/1455 |
| 2016/0324580 A1* | 11/2016 | Esterberg | | A61B 34/10 |
| 2018/0255628 A1* | 9/2018 | Yadav | | H05B 37/0272 |

\* cited by examiner

SELF-ORIENTING SURGICAL LIGHT PANEL

CROSS REFERENCE TO RELATED APPLICATIONS

The present invention claims priority to U.S. Provisional Application No. 62/370,466, filed Aug. 3, 2016, which is incorporated herein by reference, including drawings.

BACKGROUND OF THE INVENTION

Field of the Invention

The present invention relates generally to hospital lighting devices, and more specifically to a lighting system for hands-free lighting control over a surgical site.

Description of the Background

Originally, natural sunlight was used as much as possible for surgical lighting. The quality of incandescent lighting was poor and it emitted significant heat. Today, surgical lighting is provided by a light panel with a number of lamps arranged about a focal region, usually a surgical site, each of which may be adjustable to provide unobstructed lighting without shadows. Such lighting may be mounted in the ceiling of the operating room or on floor stands, and if the latter, the mounts commonly include handles to allow manual positioning and adjustment of the direction of the light source.

The International Electrotechnical Commission (TEC) publishes standard requirements for the basic safety and essential performance of surgical luminaires and luminaires for diagnosis. Some of the standards for surgical lightheads are the following:

Homogenous light: The light should offer good illumination on a flat, narrow or deep surface in a cavity, despite obstacles such as surgeons' heads or hands;

Lux: The central illuminance should be between 160,000 and 40,000 lux;

Light field diameter: Given a particle size distribution the D50 diameter should be at least 50% of D10.

Color rendition: For the purpose of distinguishing true tissue color, in a cavity, the color rendering index (Ra) should be between 85 and 100.

Backup possibility: in case of interruption of the power supply, the light should be restored within 5 seconds with at least 50% of the previous intensity, but not less than 40,000 lux. Within 40 seconds the light should be completely restored to the original brightness.

Prior art surgical lighting devices such as those described above have several important drawbacks. For most operating: rooms, lighting systems that can only be adjusted by physical contact from the surgeon or other operating room personnel is less than ideal from a contamination standpoint. Most hospitals recommend that fixtures, such as lighting and lighting stands be cleaned at the beginning and end of the surgical day, but these items are not necessarily cleaned between procedures performed on different patients, meaning that bodily fluids from one patient may be transferred to a subsequent patient if the surgeon touches a lighting fixture with his hands during both procedures without intervening sterilization.

U.S. Patent Application Publication No. 2013/0310652 to Barsoum et al. attempts to solve this problem with a method and apparatus for coordinated control of lights and devices in an operating room in which the state of the operating, room is detected from time to time during the course of a medical procedure by a machine vision system which then controls the direction of the lights in accordance with the detected state. Movement of the lighting is controlled with a control circuit.

However, a lighting system that is not directly controllable by the surgeon also suffers drawbacks in that it is not adaptable to rapid changes in the arrangement of the operating room, such as in the case of an emergency, and may not promptly respond to the surgeon's shifts in movement, or those of other operating room staff, during the course of the procedure, thereby allowing dark spots or shadows to develop, impeding the surgeon's view of the surgical site. In addition, such a system may not provide the most intensely directed spot lighting on the surgical site as may be needed for highly technical procedures.

U.S. Patent Application Publication No. 20110015492, to Mangiardi, describes a surgical lighting system in which multiple overhead light sources are independently housed and independently positionable via a powered swiveling means and support actuated by control box, which is in turn controlled by, a standalone wireless controller located at or near the surgical site. However a Mangiardi-type system also suffers from the fact that the surgeon or other operating personnel may be required to handle the controller during a procedure, which may not be practical because the surgeon for whom the light is positioned often has both hands occupied by operating during crucial parts of the procedure where re-direction of light may be required. Mangiardi also sets up a system where multiple operating room personnel may have to handle the controller device over the course of a procedure, setting up additional opportunities for contamination to be introduced to the sterile field. Finally, the presence of a stand-alone piece of equipment such as a controller at or near the surgical site may interfere with or inadvertently contact the surgical site, or be lost in the folds of surgical draping or misplaced between procedures, etc.

What is needed then is a light panel comprising a ceiling-mounted plurality of independently controlled, electronically-movable surgical lights that can provide immediate readjustment for direct spot-lighting without the need for a freestanding controller that may interfere with the operation or be left untethered near the operating site. It would also be an improvement over the prior art for, such a system to be capable of operating in a hands-free manner, in case of interruption of the power supply, the orientation and original brightness settings are restored within seconds.

The system is designed so that exposed component parts are minimized and easily sterilizable in order to minimize the risk of contamination or SSI.

SUMMARY OF THE INVENTION

Accordingly, there is, provided a system of independently-controlled spot lights suitable for use in an operating room or surgery center wherein the direction and other characteristics of each light source is controlled via Bluetooth communication with a device worn on the hand or wrist of the operating personnel. The inventive system, utilizes a programmable controller operated in accordance with software that includes programming for a "follow" function, whereby the controller will move the light sources to follow the surgeon's hands as located via the Bluetooth signal emitted from the hand-wearable device. The system may also comprise a "set" mode where the controller will focus one or more light source(s) on specified areas regardless of the movement of the surgeon's hands.

The wearable controller will be sterilizable between each use, and will provide a tethered, rather than freestanding, means of controlling the direction of the motorized light sources. In addition, the inventive system is hands-free so that the surgeon may cause spot lighting to be directed to the place where he is operating without having to remove his hands from the operating site or the sterile field.

Additional aspects of the system described herein may include means for multiple doctors or nurses to individually control one or more distinct light sources simultaneously, and for the direction of light to be controlled using a signal-emitting surgical site boundary.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

DETAILED DESCRIPTION OF THE PREFERRED EMBODIMENTS

Figure 1:
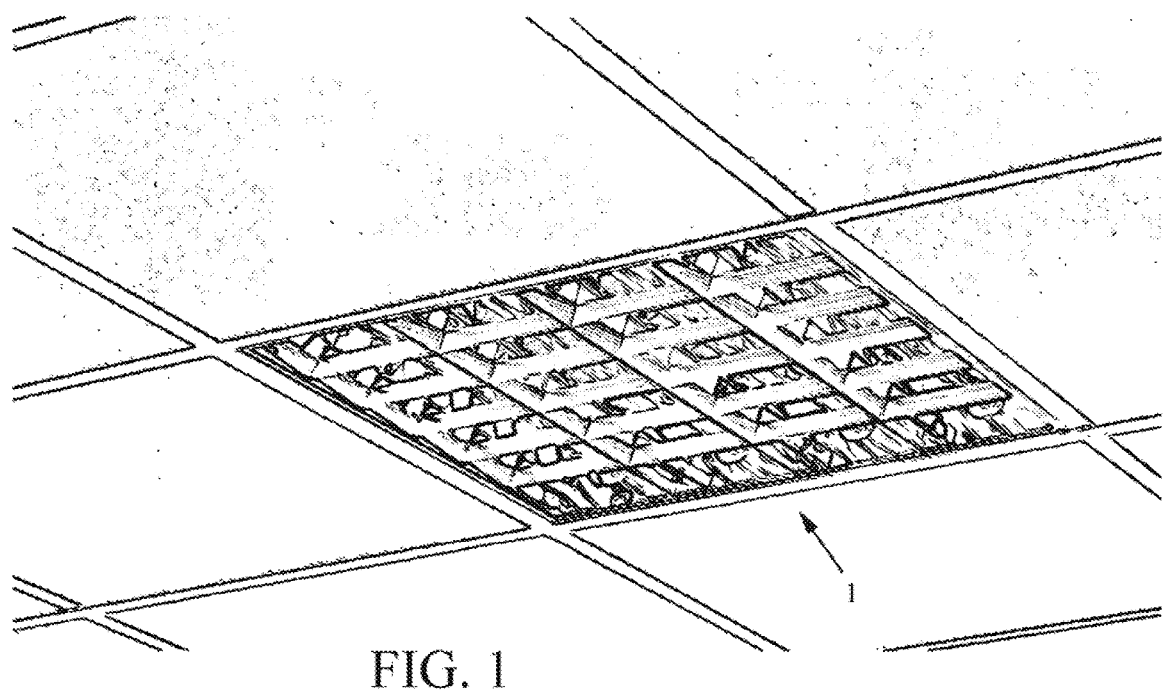
FIG. 1 is a perspective illustration of a ceiling-mounted panel lighting system 1 according to an embodiment of the invention.

Referring now to FIG. 1, an, embodiment of the ceiling-mounted panel lighting system 1 is shown. The illustrated embodiment of panel lighting system 1 is intended for a dropped panel ceiling and will be mounted in one or more panel spaces. However, one skilled in the art should understand that the lighting system 1 pray be incorporated as a freestanding lamp, wall fixture, or otherwise as a matter of design choice.

Figure 2:
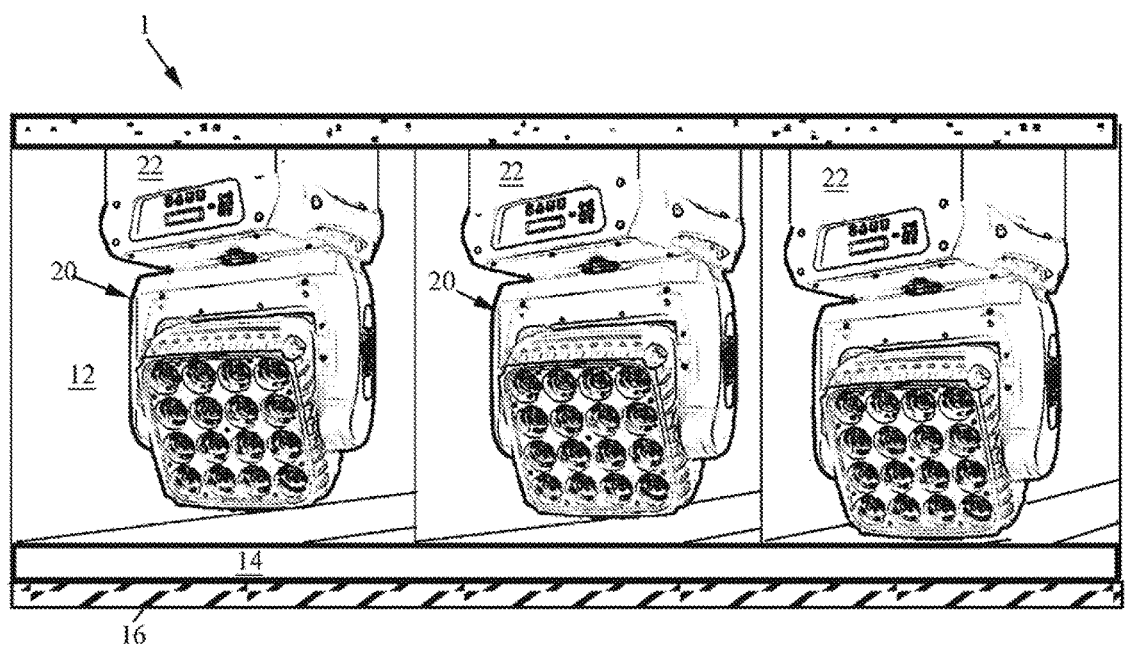
FIG. 2 is a partial side cross-section of the panel lighting system 1 of FIG. 1.

FIG. 2 is a side cross-section of the panel lighting system 1 which generally includes a rectangular electrical enclosure 12 elevated above the dropped panel ceiling and seated atop a mounting baffle 14. The baffle 14 in turn sits atop a clear glass panel 16 secured within the dropped panel ceiling. The baffle 14 provides structural support for the electrical enclosure 12 without obstructing light from a plurality of pan/tilt LED lighting assemblies 20. Each lighting assembly 20 is capable of directing a fixed-focus light beam along a selectable path, the beam having a fairly narrow field angle within a range of from 0-10 degrees. This way, when mounted in a twelve-foot ceiling; the individual beam from each lighting assembly 20 will illuminate a four-foot diameter area on a four-foot high surgical table located directly below. On the other hand, by synchronizing the pan/tilt orientations of the lighting assemblies 20, the beams can be combined into a more or less bright beam ranging upward from four feet to any desired field of illumination.

Figure 3:
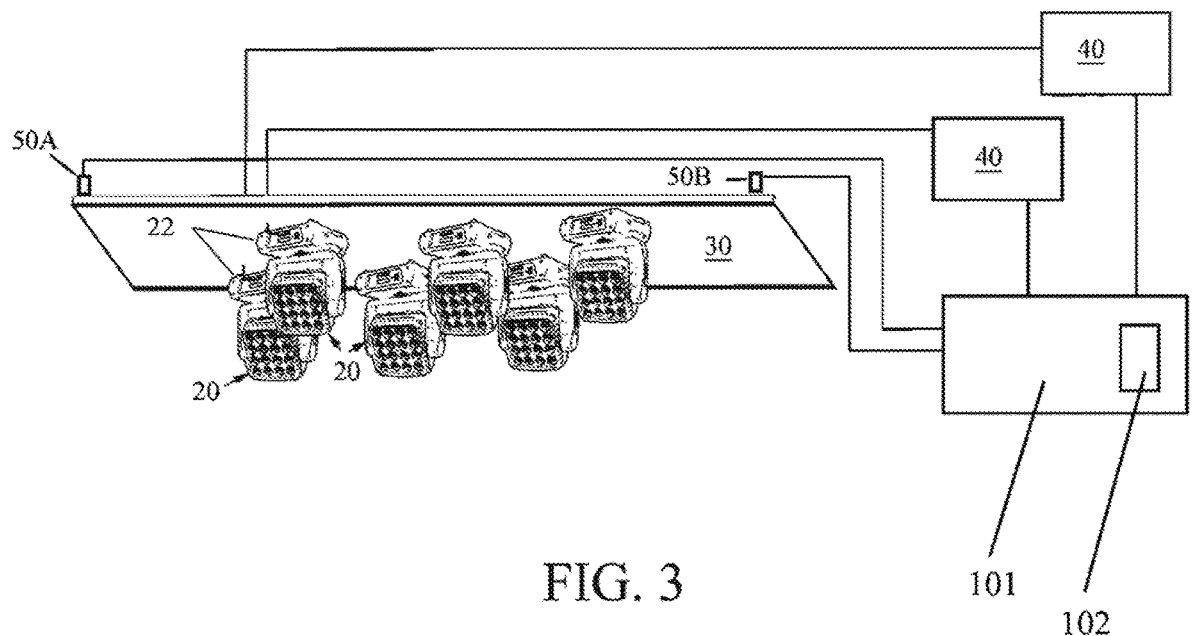
FIG. 3 is a schematic diagram of the panel lighting system 1 of FIGS. 1-2.

As depicted in FIG. 3 lighting assemblies 20 are arranged in a pattern and are surface mounted by their own individual pan/tilt bases 22 directly beneath a common printed circuit board 30 that electrically connects each to a driver 40, and all drivers 40 to a common controller 101. Each lighting assembly 20 is independently connected and controlled by its driver 40 as to light source direction, but the controller 101 runs a Bluetooth tracking software program 102 that calculates a desired illumination target and beam intensity, and collectively adjusts the pail tilt bases 22 of all lighting assemblies 20 to illuminate the designated target at the desired intensity.

Each light source 20 preferably comprises one or more high definition/high intensity light emitters, such as alight emitting diode (LED). While LED lights are preferred, it will be understood that any device capable of emitting light of a quality and strength to illuminate a surgical field within a range of approximately six-to-twenty feet could be used, including fluorescent light, high-intensity discharge (HID) bulbs or traditional incandescent light bulbs.

Further as shown in FIG. 3, each pan/tilt base 22 is a sealed, wired-controlled unit which allows continuous 360° rotation (pan) of the light source(s) as well as vertical (tilt) aiming of the light sources at any angle 25° below horizontal. A variety of suitable pan/tilt bases 22 are known such as, for example, that disclosed in U.S. Pat. No. 8,201,974 by Smith et at which is herein incorporated by reference.

The controller 101 may be mounted on the printed circuit board 30 and is preferably equipped with a processor, a computer readable non-transitory storage medium, and modular software comprising an operating system and Bluetooth tracking software program 102 stored on said non-transitory storage medium. In addition to the controller 101, two separate Bluetooth receivers 50A, 50B are mounted on the printed circuit board 30, and at least their antennas are distally spaced as far as possible. In alternative embodiments, Bluetooth receives 50A and 50B are mounted externally to printed circuit board 30 but close enough to same to be within operable connection therewith. Both Bluetooth receivers 50A and SOB are in communication with controller 101. The two Bluetooth receivers 50A and 50B will receive the radio signal from a Bluetooth hand unit 200 (to be described) located anywhere in the operating room and measure the signal received for time-of-arrival, signal strength, or both. The measured parameters are passed to controller 101 which employs Bluetooth tracking software program 102 to determine the indoor position of the Bluetooth hand unit 200 based on triangulation of the signal delay, signal strength, or both. Bluetooth tracking software program 102 is a real time location service (RTLS) solution that relies on Bluetooth beacons from hand unit 200 to determine fixed proximity or triangulated location of hand unit 200. The triangulated position comprises a set of target coordinates representing the indoor location of hand unit 200, and these target coordinates together with a desired intensity are then mapped to a set coordinated of pan/tilt instructions for each light source 20. The controller 101 outputs the individual pan/tilt instructions to each driver for translation to servo/stepper drive signals output to the respective pan/tilt bases 22. In preferred embodiments, the controller 101 does this in real time and continuously updates the target coordinates to provide a "follow" function, whereby the controller 101 will move the light sources dynamically to follow the surgeon's hands as located via the Bluetooth signal emitted from the hand-wearable device 200.

Figure 5:
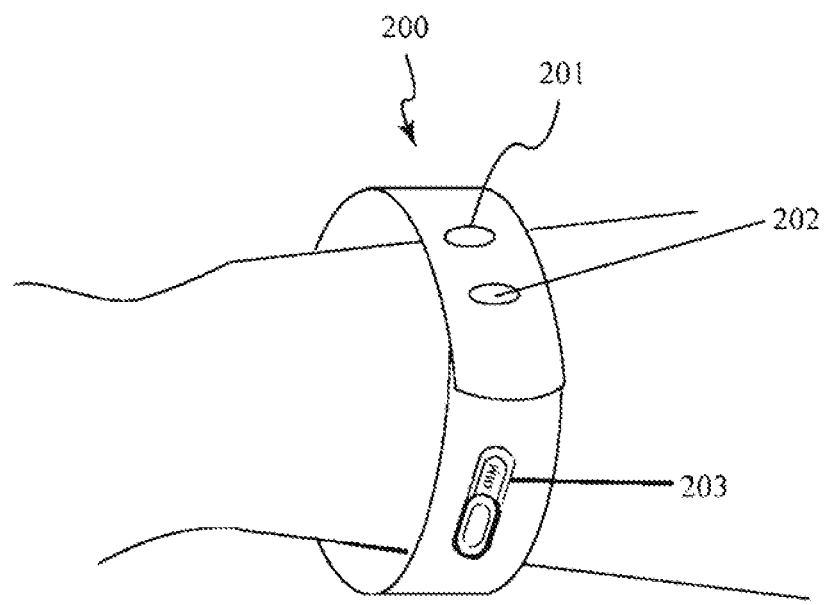
FIG. 5 is a perspective view of a hand unit 200 according to the present invention as worn on a human wrist.
Figure 6:
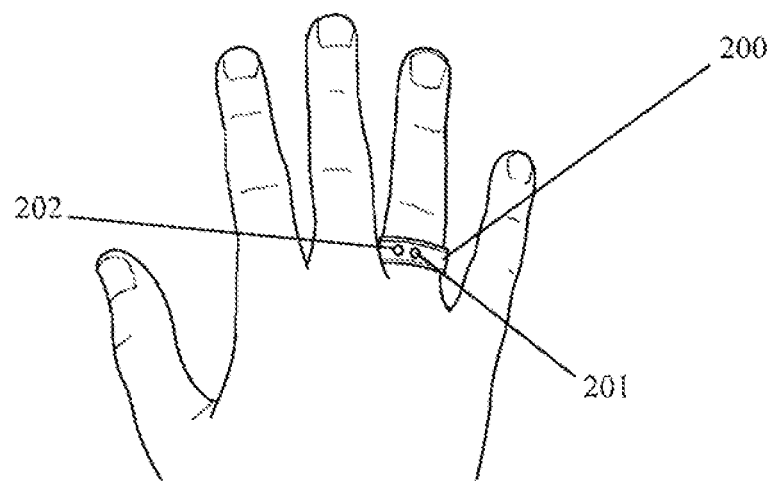
FIG. 6 is a perspective view of a hand unit 200 according to the present invention as worn on a hut an finger.

A representative hand unit 200 is shown in FIG. 6. Hand unit 200 is illustrated generally as a ring-shaped device which may be sized to be worn either as a finger ring or wrist band or otherwise securely attached to the person of a surgeon, preferably in the region of his or her hand. Hand unit preferably contains at least a transmitter 201, which is preferably a passive low-power Bluetooth signal emitting device but may any known wireless communication means including those mentioned above. In some embodiments, hand unit may also include a mode selector button 202, and a light intensity control 203. Hand unit 200 is designed to be worn by a surgeon or other operating personnel as a wrist band or ring as shown in FIGS. 5 and 6, respectively. Although hand unit 200 is shown herein as a basic ring shape, i.e. a short, hollow, open cylinder, it will be understood that hand unit 200 may be formed in any shape capable of being securely affixed to the hand of a doctor or nurse, to a point on the operating table, to a point on the patient, or to any other surface in the operating room needing a directed light. Hand unit 200 is preferably adjustable to accommodate a secure fit on any number of hand or wrist shapes or sizes. Hand unit 200 is preferably constructed of a polymer/rubber and capable of sterilization.

The inventive system operates as follows: the surgeon or other operating room, personnel (collectively, "wearer" or "wearers") wears hand unit 200 on his or her hand or wrist while performing a procedure in the operating room or healthcare facility where at least one lighting system 1 is installed or, positioned. As the wearer moves his or her hand around the operating site, one or more light sources 20 track the movement of the wearer's hand(s) by Bluetooth or other wireless signals emitted by the hand unit 200. Accordingly, transmitter 201 on hand unit 200 must be capable of transmitting a wireless signal to controller 101, which can then determine the location of hand unit 200 based on triangulation and/or proximity of the received signals. Currently, there are three localization techniques: proximity, trilateration (or, range-based) and fingerprinting (FP) [Hui L., Darabi H., Banedee P., Jing L. Survey of wireless indoor positioning techniques and systems. IEEE Trans. Syst. Man Cybern. C Appl. Rev. 2007; 37:1067-1080] Some commercially available solutions improve accuracy with a hybrid combination of these.

In preferred embodiments, the system described herein will accommodate multiple hand units 200 worn by one or more wearers by transmitting unique ID codes. Preferably, controller 101 is programmed with functionality to allow it to pair hand units 200 "on the fly" based on proximity of each hand nit to each light source 20 or other means, or pairings between hand units 200 and light sources 20 may be input into controller 101 by a technician prior to the start of a procedure. This functionality of the present system would be especially useful for cardiac or trauma surgeries, where two surgeons may be simultaneously operating on different and remote areas of a patient's body.

Figure 4:
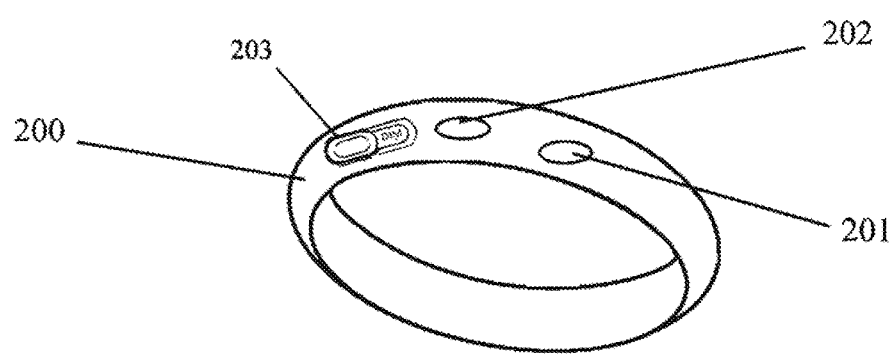
FIG. 4 is a perspective view of a representative hand unit 200 according to the present invention.

In preferred embodiments, the inventive system also has the ability to operate in both "follow" and "set" modes. As described above, in "follow" mode, signals received by controller 101 from transmitter(s) 201 on hand unit(s) 200 will be converted to instructions to controller(s) 101 to move lighting assemblies 20 so that their beams are directed towards the hand unit 200 to which they are coupled. In "set" mode, lighting assemblies 20 will remain stationary and signals received from transmitter(s) 201 on hand unit(s) 200 will not be processed by the controller 101 into instructions to controller(s) 101. To alternate between "modes", the hand unit 200 may have a button 202 (see FIGS. 4 and 5) that the wearer will push causing a wireless or Bluetooth signal to be sent to the controller 101 indicating a switch between modes. In this way, a surgeon can position his or her hand unit 200 at an area that he wants to receive constant lighting, press button 202 to swap the system's mode to "set" mode, and move about the operating room freely without interruption of lighting in the area he has chosen, in alternative embodiments, certain ones of lighting assemblies 20 may be programmed with both "set" and "follow" modes while others may be permanently set, or set by input from a technician to controller 101 prior to the procedure, to stay in a specific mode throughout the entirety of the procedure. In this way, a surgeon can switch a portion of lighting assemblies 20 to "set" mode to achieve consistent lighting of a primary operative site, while having one or more additional lighting assemblies 20 remain in "follow" mode to provide lighting to follow his hands as he moves, i.e. to retrieve a tool or to move quickly to operate on another portion of the patient's body in an emergency, and to toggle back and forth between "set" and "follow" modes at the surgeon's discretion. In still other embodiments, hand units 200 are provided with additional functionality to allow them to "lock" one or more lighting assemblies 20 in one mode to achieve this same purpose.

In still other embodiments, the direction of one or more lighting assemblies 20 in "set" mode may be preprogrammed by a technician via controller 101 prior to the start of the procedure, or by manual adjustment of the direction of lighting assemblies 20 (i.e., via remote control or by a technician operating a remote terminal inside or outside of the operating room which communicates with controller 101) without the necessity for the surgeon to hold his or her hand unit 200 in the desired direction while pressing button 202.

Operation of the intensity switch 203 to dim the intensity will serve to gradually spread the beams of the collective lighting assemblies 20 to a more diffuse and hence dimmer pattern.

Other added functionalities for the herein, described system may include means for the wearer to, control other characteristics of lighting assemblies 20, such as light color, via added buttons or dials (not shown) on hand unit 200 or by voice commands where controller 101 has means to receive and process such commands, many of which are known in the art, then convert them to instructions for controllers 101. Previously-described functionalities of the system, such as toggle between "set" and "follow" modes, may also be carried out by voice commands under this embodiment.

In alternative embodiments, hand units 200 may be replaced, or supplemented by a "ribbon" that operating room personnel can arrange around a circumference of an area that they want to be lighted. Such a ribbon may be wireless or Bluetooth™ enabled to allow it to communicate its location, along its entire length, to controller 101, may have means to emit locator "beacons" to controller 101. The ribbon may be of a fixed shape/size (i.e. square, round) or flexible to allow manipulation by personnel during the procedure that automatically results in readjustment of the lighting via the direction of lighting assemblies 20. The ribbon should be capable of being located by controller 101 even when the ribbon is placed underneath the patient or one or more layers of bedclothes, surgical drapes, clothing, etc.

While the system disclosed herein is particularly useful for use in a surgical setting, it is within the scope of the invention disclosed herein to adapt the system to use in other fields. For example, alternate forms of hand unit 200 may be envisioned whereby a unit having the functionality of the hand units 200 described here may be configured as a necklace, belt, headpiece, leg, foot or ankle mounted unit, etc. such that it may be worn by a wide variety of people who may require lighting that follows them as they move. A non-exhaustive list of additional uses for the system described herein may include: a unit worn as a belt or necklace, by a stage performer to allow lighting to follow her as she moves across a stage; a head or hand unit 200 worn by a plumber or electrician coupled with a lighting assemblies 20 (or smaller versions of appropriate light sources as known in the art) that can be removably mounted to a cabinet fixture or a headband or other device worn by the plumber; or a large-scale "ribbon" capable of encircling a portion of a construction site and coupled to stand mounted lighting assemblies 20 for lighting a construction site at night.

It should also be understood that the disclosure may be constructed of a variety of suitable surgical grade materials having suitable strength and flexibility as required by the herein-described device. This application is therefore intended to cover any variations, uses, or adaptations of the invention using its general principles. Further, this application is intended to cover such departures from the present disclosure as come within known or customary practice in the art to which this invention pertains.

I claim:

1. A system for providing light in an operating room, comprising:
   a plurality of pan/tilt articulating light sources;
   a pair of wireless receivers, each capable of receiving a wireless signal in the radio frequency spectrum;
   at least one wearable transmitting device capable of emitting said wireless signal from a target location; and
   at least one controller operatively coupled to said one or more pan/tilt articulating light sources for articulating said pan/tilt articulating light sources to provide a coordinated beam of light aimed at said target location, said controller being in communication with said wireless receiver and including software stored on non-transitory computer media and configured to triangulate said target location based on differential signal characteristics of the wireless signal received at said pair of wireless receivers.

2. The system of claim 1, wherein said at least one wearable transmitting device comprises two or more wearable devices each capable of, emitting a unique wireless signal.

3. The system of claim 2, wherein said controller is programmed to pair each of said plurality of pan/tilt articulating light sources with a single one of said two or more wearable devices based on the unique wireless signal emitted by each of said wearable devices.

4. The system of claim 2, wherein said software is configured to pair each of said plurality of pan/tilt articulating light sources with a nearest one of said two or more wearable devices based on the target location of each of said wearable devices as calculated by said software.

5. The system of claim 2 wherein said at least one controller further includes software configured to calculate a desired beam intensity of said plurality of pan/tilt articulating light sources to provide a desired illumination strength for said light sources, and to adjust said beam intensity of said plurality of pan/tilt articulating light sources.

6. The system of claim 5, wherein said at least one controller is configured to receive voice commands to adjust said beam intensity of said plurality of pan/tilt articulating light sources.

7. The system of claim 2, wherein said at least one controller is configured to operate said plurality of pan/tilt articulating light sources according to a "set" mode or a "follow" mode, wherein a position of said plurality of pan/tilt articulating light sources is fixed when placed in "set" mode.

8. The system of claim 7, wherein said at least one controller is configured to operate some of said plurality of pan/tilt articulating light sources in one of "set" or "follow" mode and others of said plurality of pan/tilt articulating light sources to be selectable between "set" mode and "follow" mode.

9. The system of claim 7, wherein each of said wearable transmitting devices includes a switch to toggle an operating mode of said controller between "set" mode and "follow" mode.

10. The system of claim 7, wherein said at least one controller is configured to receive voice commands to switch an operating mode of said at least one controller between "set" mode and "follow" mode.

11. The system of claim 2, wherein said at least one wearable transmitting device is are configured to be worn around a human wrist.

12. The system of claim 2, wherein said at least one wearable transmitting device is configured to be worn around a human finger.

13. The system of claim 2, further comprising a driver operatively connected between said controller and said plurality of pan/tilt articulating light sources.

14. The system of claim 2, wherein said plurality of pan/tilt articulating light sources are mounted in an enclosure in a ceiling of an operating room.

15. The system of claim 2, wherein
    said at least one transmitting device is a ribbon-type device,
    said target location is a location of said ribbon-type device, and
    wherein said controller includes means to triangulate said target location based on differential signal characteristics of the wireless signal received at said pair of wireless receivers.

16. The system of claim 15, wherein said at least one ribbon-type device is capable of being manipulated into a position surrounding a surgical area as an outside border.

* * * * *